(12) United States Patent  
Parent et al.

(10) Patent No.: US 8,870,929 B2  
(45) Date of Patent: Oct. 28, 2014

(54) SURGICAL DEVICES FOR THE CORRECTION OF SPINAL DEFORMITIES

(75) Inventors: Stefan Parent, Saint-Lambert (CA);  
Carl-Éric Aubin, Saint-Lambert (CA);  
Mark Driscoll, Notre-Dame-de-l'Ile-Perrot (CA)

(73) Assignee: Polyvalor, Limited Partnership Valorisation HSJ, Limited Partnership, Montreal, Quebec (CA)

( * ) Notice: Subject to any disclaimer, the term of this patent is extended or adjusted under 35 U.S.C. 154(b) by 60 days.

(21) Appl. No.: 13/446,630

(22) Filed: Apr. 13, 2012

(65) Prior Publication Data

US 2012/0290014 A1    Nov. 15, 2012

Related U.S. Application Data

(60) Provisional application No. 61/475,070, filed on Apr. 13, 2011, provisional application No. 61/475,097, filed on Apr. 13, 2011.

(51) Int. Cl.
| | |
|---|---|
| *A61B 17/88* | (2006.01) |
| *A61B 17/70* | (2006.01) |
| *A61B 17/064* | (2006.01) |

(52) U.S. Cl.  
CPC ............. *A61B 17/7053* (2013.01); *A61B 17/70* (2013.01); *A61B 17/0642* (2013.01)  
USPC ......................................... 606/279; 606/246

(58) Field of Classification Search  
USPC ........... 606/246–278, 300–321, 75, 151, 324; 623/17.11–17.16  
See application file for complete search history.

(56) References Cited

U.S. PATENT DOCUMENTS

| | | | |
|---|---|---|---|
| 5,053,005 A | 10/1991 | Borodic et al. | |
| 5,951,553 A | 9/1999 | Betz et al. | |
| 7,799,060 B2 * | 9/2010 | Lange et al. | 606/257 |
| 2003/0088251 A1 | 5/2003 | Braun et al. | |

(Continued)

FOREIGN PATENT DOCUMENTS

| | | |
|---|---|---|
| WO | 9012553 A1 | 11/1990 |
| WO | 0064360 A9 | 11/2000 |

(Continued)

OTHER PUBLICATIONS

Wittek, Operative Behandlung der Skoliose, Zeitschrift fur Orthopadische. Chirurgie, 1924. 44: p. 226-235.

(Continued)

*Primary Examiner* — Pedro Philogene  
*Assistant Examiner* — Christina Negrellirodrigue  
(74) *Attorney, Agent, or Firm* — Norton Rose Fulbright Canada LLP

(57) ABSTRACT

A method for installing a surgical device on a spine for applying corrective forces thereon comprises installing at least one anchor on a first vertebra and at least another anchor on a second vertebra. At least one connector is installed on at least one of the first and the second vertebrae. A flexible tether is fixed to one of the anchors. The flexible tether is tensioned about a surface of the at least one connector. The flexible tether is fixed to the other one of the anchors to maintain a tension in the flexible tether to apply corrective forces to the vertebrae interconnected by the tether. A method for installing a staple device with rotational joints in the vertebrae is also provided.

17 Claims, 7 Drawing Sheets

(56) References Cited

U.S. PATENT DOCUMENTS

| | | |
|---|---|---|
| 2004/0199219 A1 | 10/2004 | Dodge et al. |
| 2005/0171539 A1 | 8/2005 | Braun et al. |
| 2005/0177240 A1 | 8/2005 | Blain |
| 2006/0009767 A1 | 1/2006 | Kiester |
| 2006/0217714 A1 | 9/2006 | Serhan et al. |
| 2007/0055373 A1 | 3/2007 | Hudgins et al. |
| 2007/0173832 A1 | 7/2007 | Tebbe et al. |
| 2007/0179493 A1 | 8/2007 | Kim |
| 2007/0233084 A1 | 10/2007 | Betz et al. |
| 2007/0270836 A1 | 11/2007 | Bruneau et al. |
| 2007/0276380 A1* | 11/2007 | Jahng et al. ............ 606/61 |
| 2007/0276500 A1* | 11/2007 | Zucherman et al. ...... 623/17.16 |
| 2008/0021459 A1* | 1/2008 | Lim .................. 606/61 |
| 2009/0030518 A1 | 1/2009 | Aubin et al. |

FOREIGN PATENT DOCUMENTS

| | | |
|---|---|---|
| WO | 0103570 A2 | 1/2001 |
| WO | 0243602 A1 | 6/2002 |
| WO | 0245765 A2 | 6/2002 |
| WO | 03003901 A2 | 1/2003 |
| WO | 2005023090 A2 | 3/2005 |
| WO | 2006110767 A1 | 10/2006 |
| WO | 2007075788 A2 | 7/2007 |
| WO | 2007089979 A1 | 8/2007 |
| WO | 2007090021 A1 | 8/2007 |
| WO | 2007109470 A2 | 9/2007 |
| WO | 2007111795 A1 | 10/2007 |

OTHER PUBLICATIONS

Nachlas, I.W. and J.N. Borden, The cure of experimental scoliosis by directed growth control. J Bone Joint Surg Am, 1951. 33(1): p. 24-34.

Smith A., Von Lackum W., and W. R., An operation for stapling vertebral bodies in congenital scoliosis. J Bone and Joint Surgery, 1954. 36: p. 342-348.

Roaf, R., Vertebral growth and its mechanical control. J Bone Joint Surg [Br], 1960. 42(1): p. 40-59.

Roaf, R., The treatment of progressive scoliosis by unilateral growth-arrest. J Bone and Joint Surgery, 1963. 45B: p. 637-651.

Carpintero P., et al., Scoliosis induced by asymmetric lordosis and rotation: an experimental study. Spine, 1997. 22(19): p. 2202-2206.

Rumpf C., Lang R., and Gotz M., Evaluation of four different laser systems for a minimally invasive scoliosis treatment. J of Selected Topics in Quantum Electronics, 1999. 5(4): p. 1067-1071.

Newton P., et al., Multilevel Spinal Growth Modulation with an Anterolateral Flexible Tether in an Immature Bovine Model. Spine, 2005. 30(23): p. 2608-2613.

Newton, P.O., et al., Asymmetrical flexible tethering of spine growth in an immature bovine model. Spine, 2002. 27(7): p. 689-93.

Braun, J.T., et al., Experimental scoliosis in an immature goat model: a method that creates idiopathic-type deformity with minimal violation of the spinal elements along the curve. Spine, 2003. 28(19): p. 2198-203.

Betz R, et al., Vertebral Body Stapling Procedure for the Treatment of Scoliosis in the Growing Child. Clinical Orthopaedics and Related Research, 2005. 434: p. 55-60.

Betz, R.R., et al., An Innovative Technique of Vertebral Body Stapling for the Treatment of Patients with Adolescent Idiopathic Scoliosis: A Feasibility, Safety and Utility Study. Spine, 2003. 28(20S): p. 255-265.

Wall, E.J., et al., Endoscopic mechanical spinal hemiepiphysiodesis modifies spine growth. Spine, 2005. 30(10): p. 1148-53.

Guille J., et al., The feasibility, safety, and utility of vertebral wedge osteotomies for the fusionless treatment of paralytic scoliosis. Spine, 2003. 28(20S): p. S266-S274.

Braun, J.T., et al., Fusionless Scoliosis Correction Using a Shape Memory Alloy Staple in the Anterior Thoracic Spine of the Immature Goat. Spine, 2004. 29(18): p. 1980-1989.

Braun, J.T., et al., Creation of an Experimental Idiopathic-Type Scoliosis in an Immature Goat Model Using a Flexible Posterior Asymmetric Tether. Spine, 2006. 31(13): p. 1410-1414.

* cited by examiner

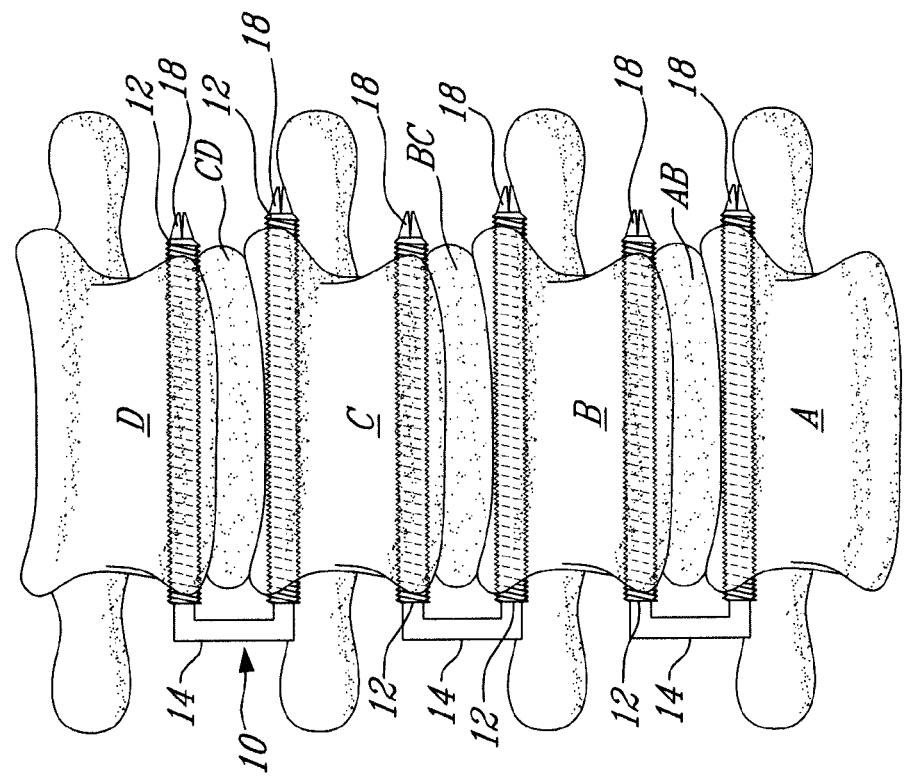
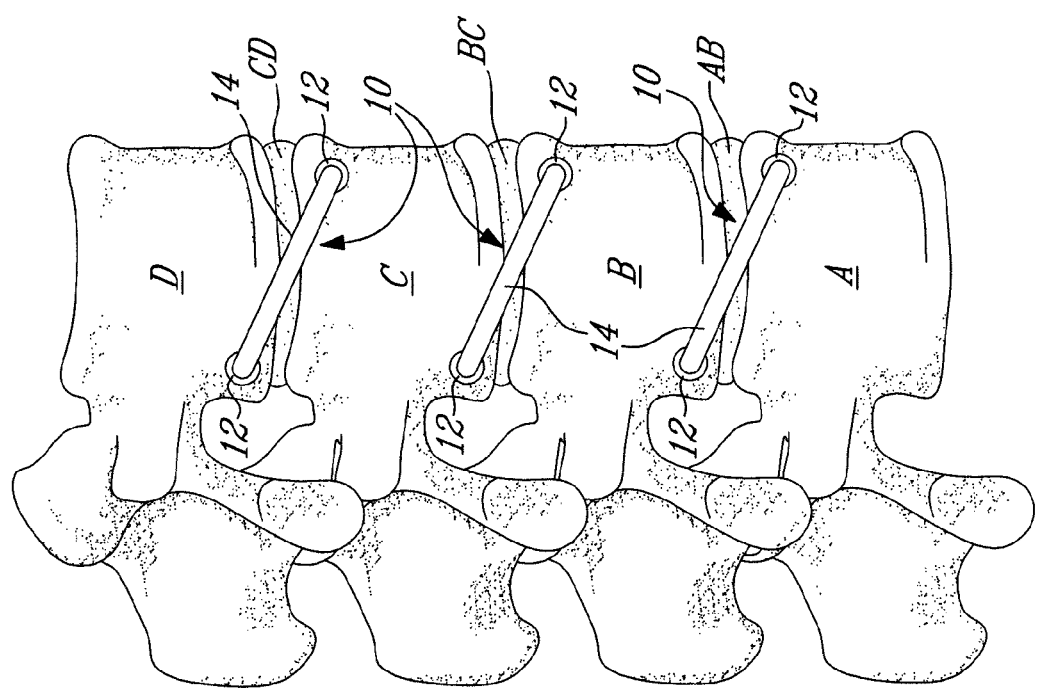

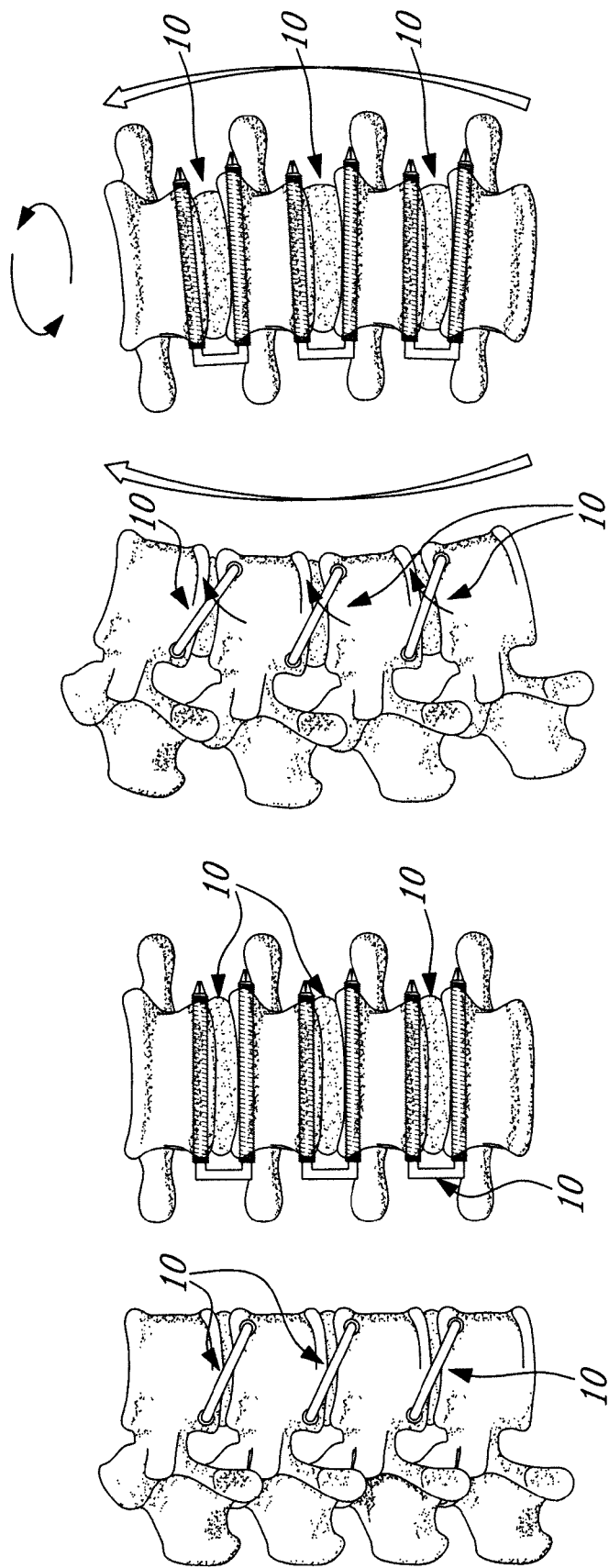

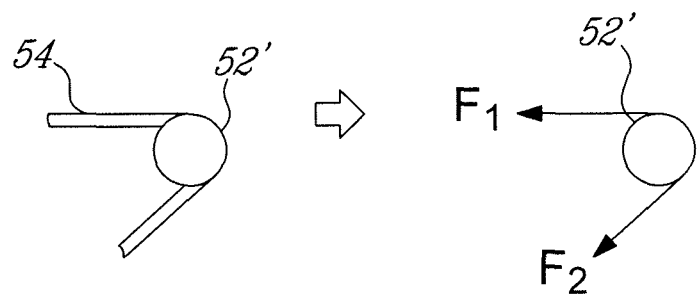
Fig-8
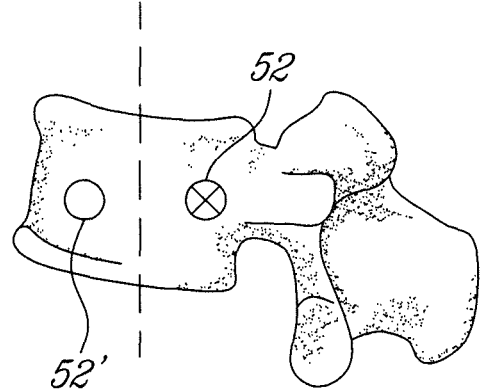
No sagittal plane influence
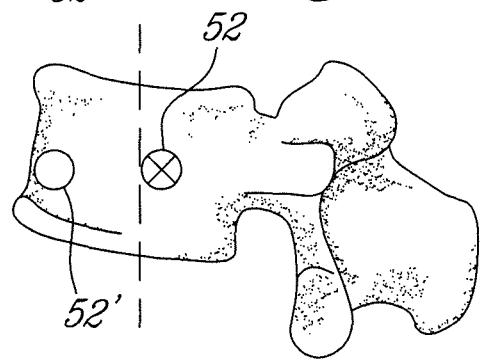
Hyperkyphosing effect
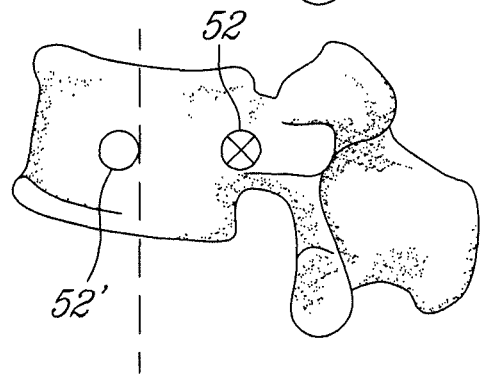
Hypokyphosing effect
Fig-9

SURGICAL DEVICES FOR THE CORRECTION OF SPINAL DEFORMITIES

CROSS-REFERENCE TO RELATED APPLICATION(S)

The present application claims priority on U.S. Provisional Patent Application No. 61/475,070, filed on Apr. 13, 2011, and incorporated herein by reference. The present application also claims priority on U.S. Provisional Patent Application No. 61/475,097, filed on Apr. 13, 2011, and incorporated herein by reference.

FIELD OF THE APPLICATION

The present disclosure relates to devices for the correction of spinal deformities, such as those used for scoliosis, hyper-/hypo-lordosis, hyper-/hypo-kyphosis, and more particularly concerns device for the correction of early onset and adolescent idiopathic scoliosis.

BACKGROUND OF THE ART

It has been known to use growth-modulating devices for the correction of spinal deformities. To date, there has been much improvement in instrumentation technologies, allowing the development of several new devices and approaches. Application of the technology is aimed at reducing, halting or, ideally, reversing the progression of curves in spines with idiopathic scoliosis. In brief, fusionless implants utilizing growth modulation may be considered as a form of internal bracing, applying static forces between pairs of vertebrae. The concept lies upon the theory that manipulation of local vertebral geometry (as a result of controlling growth) will allow the correction of global spinal curvatures that are phenotypic to spinal deformities.

These devices are based on static loads and do not provide correctional forces that are tailored to be responsive to patient positioning to provide initial and long term scoliotic correction. As a result, some prior art fusionless devices do not offer the adaptive correction in all three anatomical planes and, given their position and resulting posterior force vectors, this may lead to additional deformities such a hypokyphosis.

SUMMARY OF THE APPLICATION

It is therefore an aim of the present disclosure to provide devices for the correction of spinal deformities that address issues associated with the prior art.

Therefore, in accordance with the present application, there is provided a method for installing a surgical device on a spine for applying corrective forces thereon, comprising: installing at least one anchor on a first vertebra and at least another anchor on a second vertebra; installing at least one connector on at least one of the first and the second vertebrae; fixing a flexible tether to one of the anchors; tensioning the flexible tether about a surface of the at least one connector; and fixing the flexible tether to the other one of the anchors to maintain a tension in the flexible tether to apply corrective forces to the vertebrae interconnected by the tether.

A method for installing a surgical device on a spine for applying corrective forces thereon, comprising: installing a first hollow screw in a first vertebra; installing at least a second hollow screw in at least a second vertebrae; inserting a first prong of a staple in the first hollow screw to form a rotational joint therebetween; and inserting a second prong of the staple in the second hollow screw to form a rotational joint therebetween to apply corrective forces to the vertebrae interconnected by the staple.

BRIEF DESCRIPTION OF THE DRAWINGS

FIG. 1A is a sagittal schematic view of a spine with kinematic responsive staple devices in accordance with an embodiment of the present disclosure;

FIG. 1B is a coronal schematic view of a spine with kinematic responsive staple devices in accordance with the embodiment of the present disclosure;

FIGS. 4A and 4B are sagittal schematic view and coronal schematic view of the spine with kinematic responsive staple devices of FIGS. 1A and 1B, showing a kinematic response;

FIG. 8 is a representation of the local vector summation of a fixed screw/wire fixation provided by the wire being under tension for the spine with the tensioning-wire surgical device of FIG. 5; and FIG. 9 is a sagittal representation showing the possibility of moving the screw insertion sites anteriorly/posteriorly with respect to a sagittal midline of the vertebral body.

DESCRIPTION OF THE PREFERRED EMBODIMENTS

Figure 2:
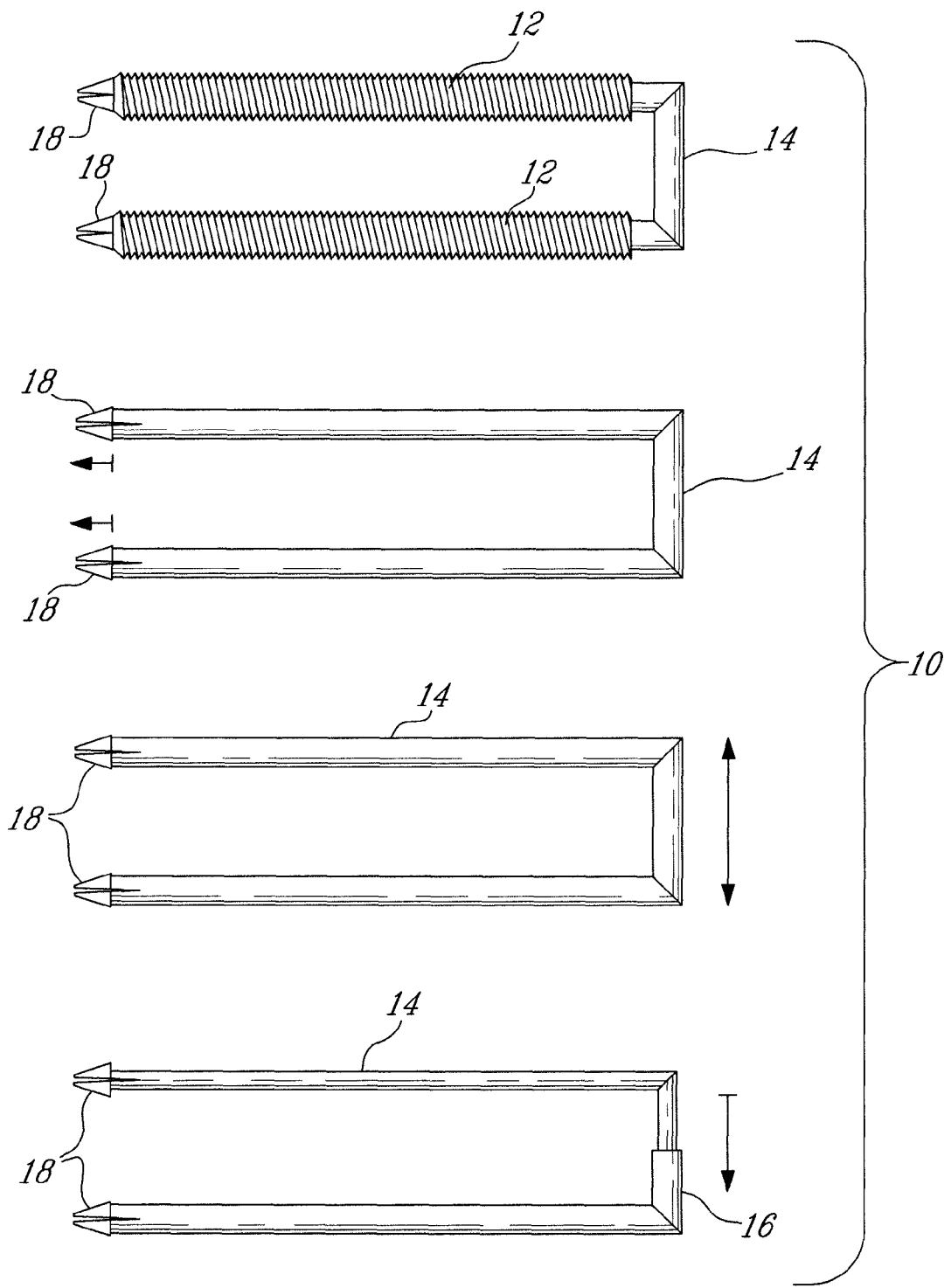
FIG. 2 is a schematic view of various configurations of the kinematic responsive staple device, in accordance with the embodiment of the present disclosure.

Referring to the drawings and more particularly to FIGS. 1A to 4B, there is illustrated kinematic responsive staple devices at 10, relative to various vertebrae A, B, C and D, separated by intervertebral discs AB, BC and CD. In accordance with the illustrated embodiment, the kinematic responsive staple devices 10 are used to correct spinal deformities via growth modulation.

Referring concurrently to FIGS. 1A, 1B and 2, the kinematic responsive staple devices 10 each comprises a pair of hollow bone screws 12 (FIG. 2) inserted into the anterior vertebral bodies on the convexity of the spinal deformity, and connected to one another with a staple 14. This configuration allows controlled force vectors between adjacent vertebrae. These forces may provide initial and long term correction of the spinal deformity through the introduction of initial tensions in the staple 14 obtained for instance using surgical instrumentation (using scoliosis curve reduction) and by manipulating vertebral morphology via growth modulation.

A relative motion is allowed between the staple 14 and the hollow bone screws 12, as each leg of the staple 14 forms a rotational joint with its respective hollow bone screw 12, allowing one rotational degree of freedom. As best seen in FIG. 1A, the staple 14 attaches to the bone screws 14 at an angle relative to a cranial-caudal axis of the patient, to provide both coronal and axial correction while providing further deformity improvement if growth is to occur.

The lateral position of the attachment points of the staple device 10 with respect to the central spinal curve allows the control of the sagittal profile. The kinematic responsive staple device 10 (the device 10 forces change as a function of patient movement) provides an environment that will generally prevent segmental fusion between adjacent vertebrae. In addition, the degree of mobility maintained by way of the rotational degrees of freedom may encourage the maintenance of healthy intervertebral discs, which may be a common disconcert with fusionless growth modulating devices as they target the pediatric population.

Referring to FIG. 2, there is illustrated different components of the kinematic responsive staple device 10. For instance, the hollow bone screws 12 are shown as being installed on the staple or staple body 14, thereby forming rotational joints. According to another configuration, the staple body may also be of adjustable length as shown at 16 (i.e., one way reduction of staple body made available for intra-operative adjustment), or be available in different lengths (length being the distance between the staple prongs). The staple prongs may consist of a clip 18 to latch onto the hollow bone screws 12. Considering the invasive nature of the procedure, the components of the staple device 10 are made of appropriate materials for such use.

Figures 3A, 3B:
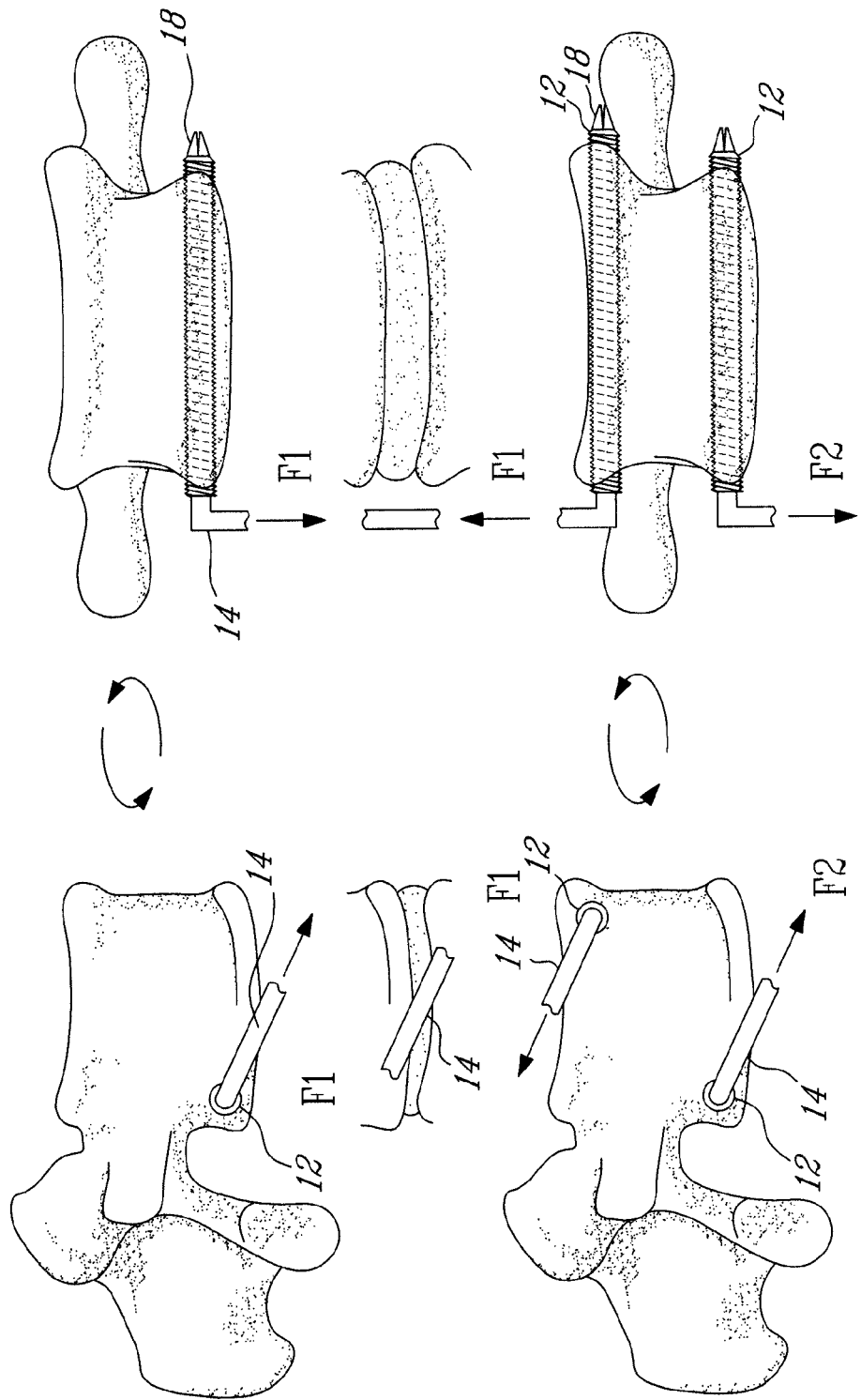
FIG. 3A is a sagittal schematic view of a free body diagram achieved on the spine with kinematic responsive staple devices of FIG. 1A.
FIG. 3B is a coronal schematic view of a free body diagram achieved on the spine with kinematic responsive staple devices of FIG. 1B.

Referring to FIGS. 3A and 3B, there is illustrated free body diagrams achieved with the arrangement of the staple devices 10 on the spine as proposed in FIGS. 1A and 1B, respectively. Net forces are exchanged between adjacent vertebrae, with the magnitude and direction of the force vectors being alterable as desired, for instance by patient movement. These forces may provide the desired three-dimensional correction of the deformity under consideration (on a short or long term scale). Moreover, the arrangement of the staple devices 10 on the spine may offer local relative motion between adjacent vertebrae by the rotational degrees of freedom provided. In turn, force vectors depicted in FIG. 3 will be altered according to patient movement.

Referring to FIGS. 4A and 4B, there is illustrated the kinematic response achieved on the spine with the arrangement of staple devices 10 proposed in FIGS. 1A and 1B, respectively. Under the configuration proposed in FIGS. 1 and 1B, the instrumented spine would allow for local motion to occur between vertebrae. As reported in FIGS. 4A and 4B, this respective mobility would entail the addition of corrective forces to the deformity at hand.

In one embodiment, the kinematic responsive staple device 10 is used for the fusionless correction of adolescent idiopathic scoliosis by means of growth modulation, and seeks to correct spinal deformities via fusionless instrumentation and growth modulation in all anatomical planes, thereby allowing the three-dimensional control between adjacent vertebrae. The degrees of freedom between screws 12 and staple 14 as illustrated in FIGS. 1A, 1B and 2 is thus responsive to patient movement.

This use of mechanically independent links from one another while maintaining a degree of freedom between staple and bone screws allows a relative motion to be achieved between adjacent vertebrae. In a common scoliotic deformity—i.e., right thoracic curve with vertebral rotation into the convexity—the staple devices 10 would be positioned on the convex portion of the spine.

In order to install the staple devices 10, two of the hollow bone screws 12 are inserted per vertebra. Once the bone screws 12 are inserted, the dimension of the staple 14 is selected or adjusted to a desired length while imposing the desired local initial correction.

Then, staples 14 are attached to superior-posterior and inferior-anterior portions of vertebrae (with respect to the intervertebral disc) as shown in FIG. 1A. The staples 14 are attached to the vertebrae by being inserted into the bone screws 12. For instance, the staples 14 may be secured with an automatically locking clip 18 located at an end of the staple prongs, as shown in FIG. 2. According to an embodiment, the staples 14 may be surgically inserted into the hollow bone screws 12 after all screws are secured in their final positions. In an embodiment, a length of the adjustable staples 16 may be adjusted after insertion.

The staple devices 10 as arranged in the spine as in FIGS. 1A and 1B may allow coronal plane correction, net axial correction, and, as desired, sagittal manipulation. Coronal plane correction (spinal realignment in this anatomical reference plane) is achieved by compressive forces on the convexity of the spine by forces introduced with the staples 14. Axial correction of scoliotic deformities must ensure that each vertebra is rotated towards the concavity of the deformity and, thus each successive vertebra rotated in the same direction (regarding vertebra located in the curvature only since vertebrae outside the region of curvature may tend to rotate the other way as a method of compensation). Thus, one appropriate method for correcting derotation problems of this nature (scoliotic derotation) is to achieve successive axial correction (transverse plane). Sagittal manipulation depends on the position of the device with respect to the midline of the anterior vertebral bodies. Such corrections may be achieved with the staple devices 10 as demonstrated in the free body diagrams of FIGS. 3A and 3B.

Initial correction in the coronal plane is achieved by having the staple devices 10 instrumented to the convexity of the spine. This provides a net compression on the convex portion of the spine that will result in realignment of the scoliotic deformity. Initial correction provided by the staple devices 10 involves compression on the convex portion of the intervertebral discs. Initial axial correction resides on the magnitude of the force vectors involved. The upper vertebra in FIGS. 3A and 3B has one force vector. Thus, a net rotation (positive torque) is achieved around the z axis. The lower vertebra has two force vectors present as it was instrumented with two staple devices 10. As long as F2>F1, this configuration will achieve a net axial rotation around the z axis in the same direction as the superior vertebra (positive torque). This configuration may be repeated for as many levels as desired.

A manipulation of the sagittal plane may be achieved by simply positioning the staple device 10 more anteriorly or posteriorly with respect to the vertebral body. This positional alternation will induce a greater compressive force on the anterior or posterior portion of the intervertebral discs and thus provide an initial manipulation of the spinal alignment in this anatomical reference plane.

Long term correction via growth modulation may be achieved as follows. The forces discussed above providing initial corrections gained pre-operatively will remain over time and allow a further correction to the spinal alignment by means of selective growth modulation (i.e., bone growth under increased compression will stop or grow at a slower rate). As demonstrated in FIGS. 3A and 3B, the intervertebral discs, acting as enclosed growth plates, will be submitted to the identified force vectors. Such application of forces will result in altered vertebral growth which will complement the previously discussed initial correction. More specifically, in one aspect, due to increased compressive forces on the convexity of the spine, vertebral growth in this region will be slowed or halted. Moreover, if convex vertebral growth continues despite the presence of the staple devices 10, the staple orientation, and consequently its force vectors, would only allow such growth to occur by inducing supplementary correction of vertebral derotation (regardless of the aforementioned efforts to halt convex growth, previously published attempts at fusionless growth modulation for the correction of scoliotic spines indicate that convex growth continues at a slower rate—a factor accounted for in the staple device 10 described herein). This occurs as a result of the rigid link that would respond to the attempted expansion from convex growth by increasing the force vectors identified above. This increased force leads to additional positive corrective torques in the z axis. In a similar manner to long term correction in the coronal plane via targeted growth modulation, sagittal long term correction could be achieved if desired.

In addition to initial and long term correction that may be performed using the staple devices 10 described herein, the maintenance of degrees of freedom between the staple 14 and the bone screws 12 in combination with its positioning on the vertebral body allows responsive kinematics to take place. More specifically, the staple devices 10 maintain segmental vertebral motion. Although corrective forces are provided by the device 10, they are neither immobile nor static—they are kinematic and responsive. In other words, for example, if spinal flexion was induced by the patient, the device 10 would react to this kinematic movement as demonstrated in FIGS. 4A and 4B. As illustrated, a spinal flexion would augment tension in the staple 14 which, consequently, would provide a positive axial torque (which, as demonstrated, would further provide axial derotation) and a lateral compression adjacent to device 10.

The kinematic responsive staple device 10 is a fusionless growth modulating apparatus that actively seeks to obtain correction of spinal deformities in all three anatomical planes, as opposed to some prior art fusionless growth modulating technologies solely targeting the coronal plane, and in which secondary influence on sagittal and transverse planes may be speculated to occur as secondary effects to the coronal manipulation. In addition, the kinematic responsive staple device 10 permits local vertebral correction independently of its adjacent vertebral bodies. Therefore, during instrumentation, certain vertebral body orientations may be corrected more or less than others, as desired. Moreover, the proposed device 10 is positioned in a matter to achieve additional axial correction if additional growth is to occur.

Referring now to FIGS. 5-9, there is illustrated another embodiment in accordance with the present disclosure, featuring a tensioning-wire surgical device 50 aiming at correcting three-dimensional spinal deformities via growth modulation. The surgical device 50 comprises anchors such as bone screws 52/52' inserted into the anterior vertebral bodies on the convexity of the spinal deformity, and are attached to one another with a wire 54. As alternatives to screws 52, other anchors could be used such as posts, etc. The wire 54 may consist of any appropriate biomedical material, such as stainless steel (e.g., 316L), nitinol or polyethylene, among other possibilities). This surgical device 50 allows the transfer of controlled force vectors between adjacent vertebrae. These forces may provide initial and long term correction of the spinal deformity through the introduction of initial tensions obtained during surgical instrumentation and the manipulation of vertebral morphology via growth modulation, respectively. Two or more independently fixed screws are provided per vertebra, with fixed anchor screws 52 and connector screws 52', and are linked to the same wire 54. The screw 52/wire 54 links is fixed while the other(s), on the same vertebra, is (are) loose, thereby allowing sliding of the wire 54 about the screw 52'. This arrangement allows the relative motion between adjacent vertebrae, with the tensioning of the wire 54 selectively constraining some of the motion. More specifically, the surgical device 50 allows the control and adjustment of both the magnitude and direction of the force vectors between adjacent vertebrae. Thus, the wire tension between each set of vertebrae is independent of the wire tension in adjacent vertebrae, allowing the localized correction of spinal deformities.

The tensioning-wire surgical device 50 seeks to correct spinal deformities via fusionless instrumentation and growth modulation in all anatomical planes. The tensioning-wire surgical device 50 permits the transfer of 3D control between adjacent vertebrae, by way of the screw and wire fixation pattern as illustrated in FIG. 5.

Figure 5:
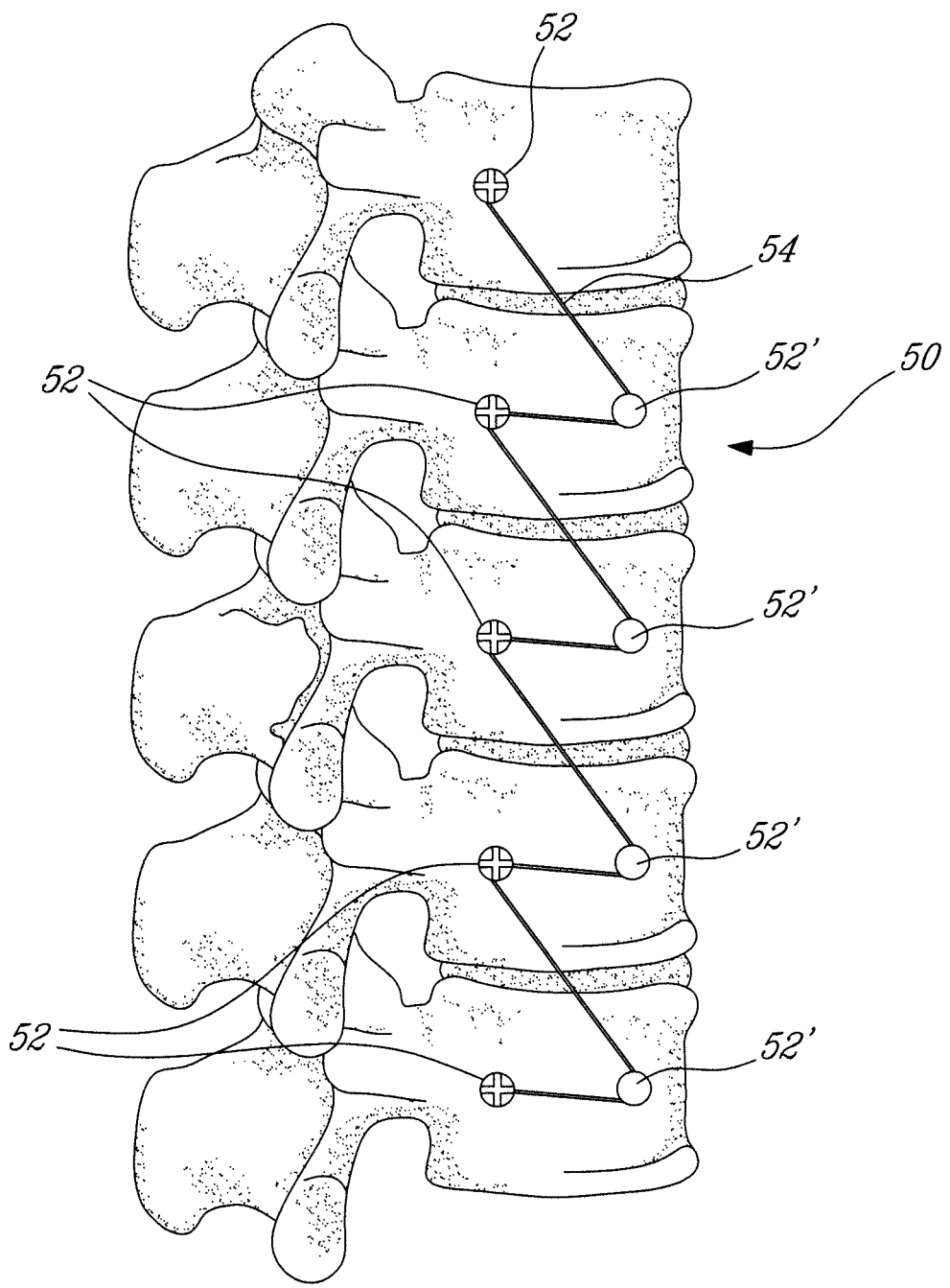
FIG. 5 is a sagittal schematic view of a spine with tensioning-wire surgical device in accordance with another embodiment of the present disclosure.
Figure 6:
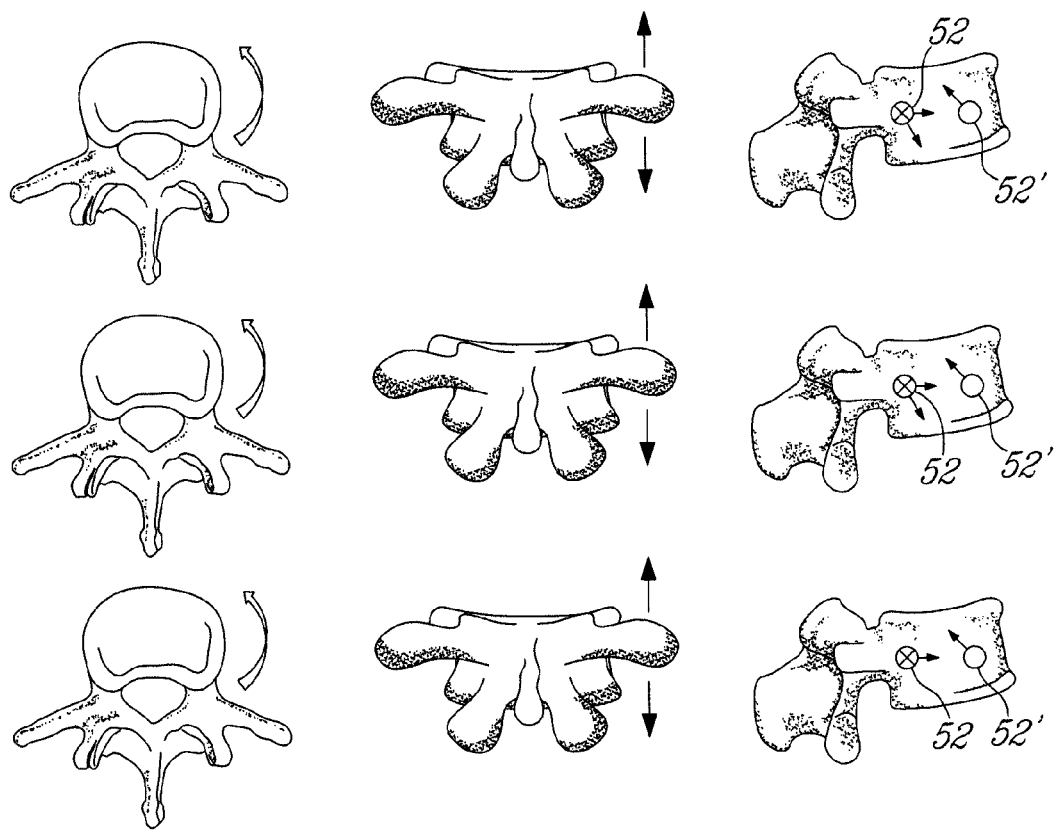
FIG. 6 is a schematic representation of the transverse, coronal and sagittal force vectors in free body diagram format, for spine with the tensioning-wire surgical device of FIG. 5.

FIG. 5 demonstrates an exemplary combination of wire/screw fixation that would allow the relative motion to be translated between a given vertebral body and the inferior and/or superior vertebrae. As mentioned previously, two or more screws 52 are independently fixed per vertebra on the convexity of the spinal curvature. The configuration of FIG. 5 may be altered and adjusted to achieve various corrective forces in the anatomical planes of choice. The configuration of FIG. 5 may provide a compression on the convexity of the spine in the coronal plane and a corrective torque in the transverse plane (aimed at correcting vertebral derotation present in spinal deformities), while sagittal manipulation may be achieved as desired. The resulting force vectors, associated to the configuration of FIG. 5, are detailed in the free body diagrams of FIG. 6. It is shown that a net successive derotation torque may be achieved in transverse plane. A compression may be obtained at all instrumented levels in the coronal plane, while sagittal manipulation may be performed as indicated in FIG. 5.

Figure 7:
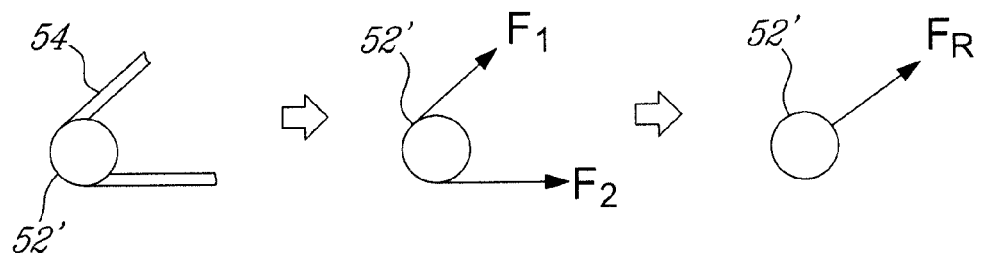
FIG. 7 is a representation of the local vector summation of a sliding screw/wire fixation provided by the wire being under tension for the spine with the tensioning-wire surgical device of FIG. 5.

FIG. 7 details the free body diagrams achieved in a sliding fixation. Because the same wire 54 is used, the tension in the wire 54 (shown by F1 & F2) on both ends around the connection is equal and thus the resultant force will always be in the same direction while the magnitude may vary.

FIG. 8 demonstrates the free body diagram of a fixed connection. The wire/screw connection is fixed and therefore F1 F2. In practice, and during surgical instrumentation, this concept will allow the surgeon to achieve local corrections where each vertebral level may be corrected independently from one another.

As shown in FIG. 9, the positioning of the screw insertion sites may be adjusted anteriorly or posteriorly with respect to the sagittal midline of the vertebral body. This adjustment is in consideration of the immediate and/or long term modification of the sagittal plane with the tensioning-wire surgical device 50. A variation of the screw location on the anterior vertebral body with respect to its sagittal midline may achieve control over kyphotic deformities.

In order to install the tensioning-wire surgical device 50, sets of screws 52 and 52' are installed on the vertebral body of each selected vertebra, after the bone has been drilled and possibly tapped. The sets of screws 52 and 52' are installed according to a predetermined configuration, for instance with a positioning of the screws 52 and 52' considering the conditions illustrated in FIG. 9.

A first wire 54 (a.k.a., a tether) is then installed by being fixed to a first one of screws 52, and by surrounding in sliding contact the screw 52' of one of the vertebrae. The opposed end of the wire 54 is then pulled and fixed to the other one of the screws 52, with the desired tension. An adjustment step may be performed to adjust the tension in any of the sets of screws 52-52'-52.

These steps are repeated for each vertebra having screws thereon. It is considered to use a single wire 54, and in such a case, the user may begin installing the wire 54 on the screws 52/52' of the bottommost or uppermost vertebrae. The free exceeding end(s) of the wire 54 is then cut. It is also considered to selectively angularly couple the flexible tether with a generally equivalent angle, in a zig-zag pattern as shown in FIG. 5. A key aspect of the tensioning-wire surgical device 50 that differentiates it over prior art (e.g., US Patent Application Publication No. 2005/0216004) is that the angle is maintained generally constant when vertebrae are serial connected with the surgical device 50. Mechanically, reversing the angle of the adjoining member/link between screws (as proposed in US 2005/0216004 A1) may simply remove any derotational forces provided as a result of opposing reaction forces at adjacent levels. FEM analyses may indicate that a spine using the surgical device 50 create rotational forces in the same direction for each adjacent vertebra. Another novel aspect of the surgical device 50 is the use of anchors 52 and connectors 52' for the same tether 54 on the same vertebral body. This may allows directing the active force vector to be adjusted as desired by selective anchors 52 and connectors 52' positioning.

The tensioning-wire surgical device 50 may permit local vertebral correction independently of its adjacent vertebral bodies. Therefore, during instrumentation, certain vertebral body orientations may be corrected more or less than others as desired.

The invention claimed is:

1. A method for installing a surgical device on a spine for applying corrective forces thereon, comprising:
    installing at least one anchor on a first vertebra and at least another anchor on a second vertebra;
    installing at least one connector directly on at least one of the first and the second vertebrae at a location spaced from a linear axis linking the at least one anchor of the first vertebra and the at least one anchor of the second vertebra;
    fixing a flexible tether to one of the anchors;
    tensioning the flexible tether about a surface of the at least one connector, wherein tensioning the flexible tether comprises tensioning the flexible tether between a first pair of vertebrae independently of the tensioning of the flexible tether between a second pair of vertebrae; and
    fixing the flexible tether to the other one of the anchors to maintain a tension in the flexible tether to apply corrective forces to the vertebrae interconnected by the tether.

2. The method according to claim 1, wherein installing anchors and connectors comprises installing the anchors and the connectors to the vertebral bodies of the vertebrae.

3. The method according to claim 1, wherein installing anchors and connectors comprises installing the at least one connector anteriorly of the anchor on the same vertebra.

4. The method according to claim 1, installing anchors and connectors comprises positioning the anchors and connectors relative to a sagittal midline of the vertebral bodies as a function of a hyper-/hypo-kyphosing effect.

5. The method according to claim 1, wherein a sequence of installing anchors and connectors and fixing and tensioning the flexible tether are repeated for a succession of vertebrae.

6. The method according to claim 5, wherein the sequence is effected with a single one of the flexible tether.

7. The method according to claim 1, wherein tensioning the flexible tether about a surface of the at least one connector comprises forming a sliding joint between the surface of the connector.

8. The method according to claim 1, wherein installing anchors and connectors comprises making holes in the vertebrae and inserting therein the anchors and the connectors.

9. The method according to claim 1, wherein fixing the flexible tether at one end comprises selectively angularly coupling the flexible tether with a generally equivalent angle.

10. A method for installing a surgical device on a spine for applying corrective forces thereon, comprising:
    installing a first longitudinally hollowed screw in a first vertebra;
    installing at least a second longitudinally hollowed screw in at least a second vertebrae, the first and second longitudinally hollowed screws each having a distal end, the first and second longitudinally hollowed screws forming an angle relative to a cranial-caudal axis;
    inserting a first prong of a staple in the first longitudinally hollowed screw to form a rotational joint between a distal end of the first prong and the distal end of the first longitudinally hollowed screw; and
    inserting a second prong of the staple in the second longitudinally hollowed screw to form a rotational joint between a distal end of the second prong and the distal end of the second longitudinally hollowed screw to apply corrective forces to the vertebrae interconnected by the staple.

11. The method according to claim 10, wherein installing longitudinally hollowed screws comprises installing the longitudinally hollowed screws laterally into the vertebral bodies of the vertebrae.

12. The method according to claim 10, wherein installing longitudinally hollowed screws comprises installing an upper one of the longitudinally hollowed screws posteriorly in the sagittal plane of the vertebral body, and installing a lower one of the longitudinally hollowed screws anteriorly in the sagittal plane of the vertebral body.

13. The method according to claim 10, wherein a succession of installing longitudinally hollowed screws and inserting the prongs of the staple is repeated for a succession of vertebrae.

14. The method according to claim 13, wherein installing longitudinally hollowed screws comprises installing an upper one of the longitudinally hollowed screws posteriorly in the vertebral body, and installing a lower one of the longitudinally hollowed screws anteriorly in the vertebral body for all staples of the succession.

15. The method according to claim 13, wherein installing the longitudinally hollowed screws and inserting the staples in the succession comprises inserting the prongs of two different ones of the staples in a same vertebra.

16. The method according to claim 10, wherein installing the longitudinally hollowed screws comprises making holes in the vertebrae and screwing the longitudinally hollowed screws therein.

17. The method according to claim 10, wherein inserting the prongs in the longitudinally hollowed screws comprises automatically clipping the prongs to the longitudinally hollowed screws.

* * * * *